US00PP14773P2

(12) United States Plant Patent
Bourne

(10) Patent No.: US PP14,773 P2
(45) Date of Patent: May 11, 2004

(54) GRAPEVINE PLANT NAMED '13-21-12'

(50) Latin Name: *Vitis vinifera*
Varietal Denomination: 13-21-12

(75) Inventor: Timothy F. Bourne, Visalia, CA (US)

(73) Assignee: Sunview Vineyards of California Inc., Delano, CA (US)

( * ) Notice: Subject to any disclaimer, the term of this patent is extended or adjusted under 35 U.S.C. 154(b) by 0 days.

(21) Appl. No.: 10/280,675

(22) Filed: Oct. 24, 2002

(51) Int. Cl.[7] ..... A01H 5/00

(52) U.S. Cl. ..... Plt./207

(58) Field of Search ..... Plt./207

*Primary Examiner*—Kent Bell
(74) *Attorney, Agent, or Firm*—Jondle & Associates PC

(57) ABSTRACT

This new grape plant '13-21-12' is new and different because of its unusual shape, late ripening and very large berry size. It differs from the 'Thompson Seedless' variety, from which it descends, by having a much larger berry size, berries with a tougher skin and looser cluster. It somewhat resembles the 'Calmeria' variety, from which it also descends, by having a seedless berry and larger berry size upon application of exogenous gibberellic acid.

2 Drawing Sheets

Genus and species: *Vitis vinifera.*

BACKGROUND AND SUMMARY OF THE INVENTION

The new grape plant named '13-21-12' is of *Vitis vinifera* parentage and resulted from a twenty year breeding program which had as its goal the development of a late ripening, white, seedless table grape. The female parent was the variety 'Calmeria' (unpatented). The male parent of the cross is an unnamed, seedless grapevine resulting from a series of crosses involving 'Emperor' (unpatented), 'Thompson Seedless' (unpatented), and 'Calmeria' (unpatented). The hybridization resulting in '13-21-12' was made near McFarland, Calif. in 1992. The seedling was selected from a population of 218 seedlings of like parentage in 1996. It was then propagated by cuttings and grafting to 'Freedom' (unpatented) rootstock. Those resulting plants were stable and typical of the original vine.

COMPARISON WITH PARENTAL CULTIVAR

The new grape plant named '13-21-12' somewhat resembles the standard variety 'Calmeria' (unpatented), its female parent, but differs from it by bearing seedless berries. The new variety resembles its unnamed male parent but differs from it by bearing elongate rather than spherical berries.

DESCRIPTION OF THE FIGURES

The accompanying drawings illustrate the following.

DETAILED BOTANICAL DESCRIPTION OF THE INVENTION

Figure 1:
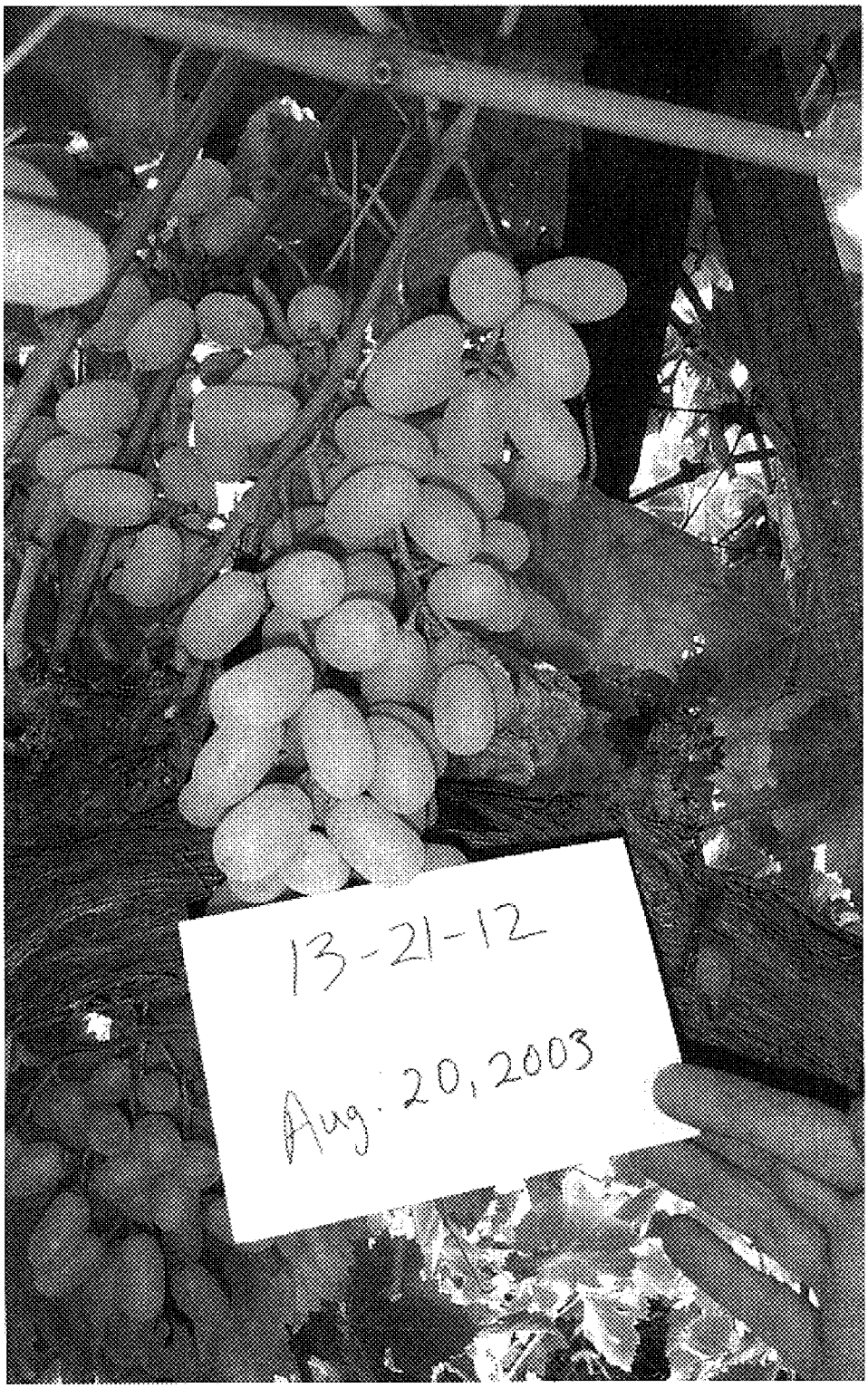
FIG. 1 shows a fruit cluster at harvest.
Figure 2:
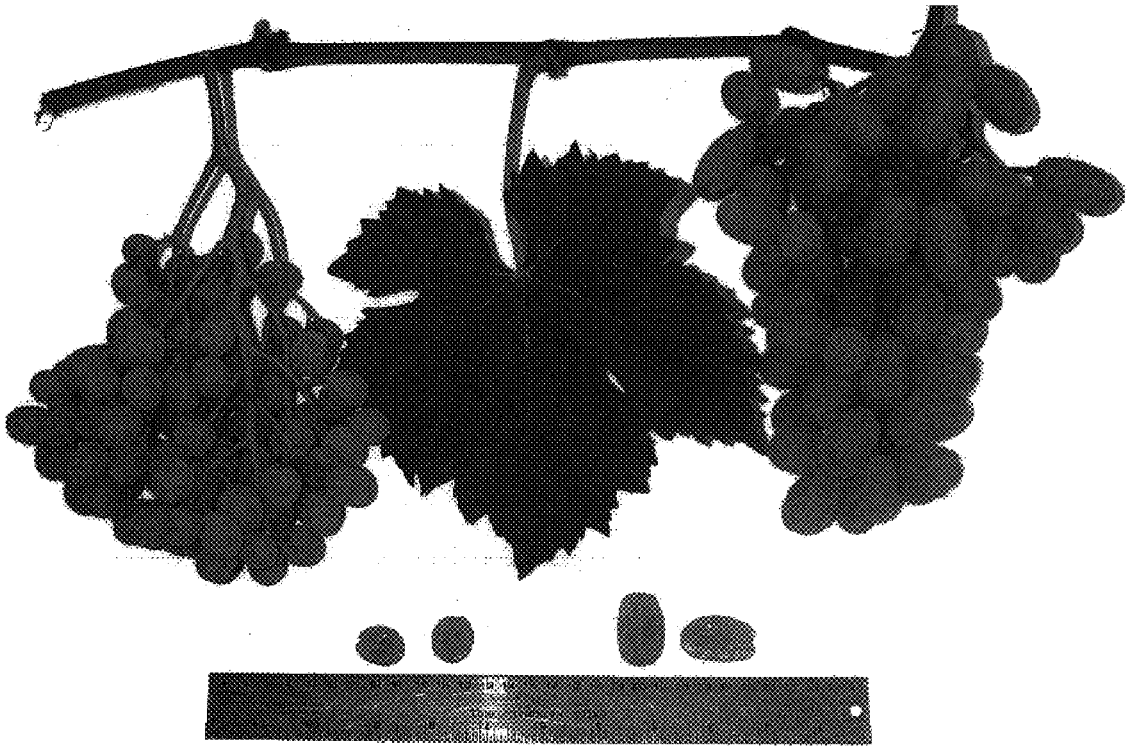
FIG. 2 shows a cane, leaf, natural fruit cluster (left) and fruit cluster following gibberellic acid applications (right).

The following description of grapevine '13-21-12' contains references to color names taken from the Munsell Color Chart for Plant Tissues, published by Munsell Color, New Windsor, N.Y. Descriptors used herein conform to those set forth by the International Board for Plant Genetic Resources Institute Grape Descriptors (Vitis spp.) of 1983 and/or 1997 which were developed in collaboration with the Office International de la Vigne et du Vin (OIV) and the International Union for the Protection of New Varieties of Plants (UPOV) and published in Descriptors for Grapevine (Vitis spp.) (Anonymous, International Plant Genetic Resources Institute, 1997, ISBN 92-9043-352-3).

Descriptions of the new invention apply to vines of '13-21-12' grown on 'Freedom' rootstock at a density of 1,537 vines per hectare grown in Kern County, Calif. in 2001. These vines were in their first year of full production having been planted in 1998. These descriptions are believed to apply generally to the new variety grown under similar circumstances elsewhere:

VINE

General:

*Vigor.*—Medium, vines spur pruned and thinned to 32 shoots per vine average 259 cm of growth per cane.
*Density of foliage.*—Dense.
*Hardiness.*—Observed hardiness to 0 C.
*Productivity.*—Very productive when spur pruned, up to 58,627 kg./hectare.
*Rootstock.*—Freedom.

Trunk:

*Shape.*—Broadly elliptical.
*Straps.*—Long, split.
*Surface texture.*—Shaggy.
*Trunk circumference.*—20.2 cm. at 1 meter height.
*Inner bark color.*—5YR 4/8.
*Outer bark color.*—2.5Y 5/2.

LEAVES

Mature leaves:

*Average blade length.*—14.6 cm.
*Average blade width.*—18.2 cm.
*Size of blade.*—Medium to large.
*Shape.*—Pentagonal.

*Anthocyanin coloration of main veins on the upper side of the blade.*—Absent.
*Mature leaf profile.*—Flat.
*Blistering surface of blade upper surface.*—Absent.
*Leaf blade tip.*—In plane of the leaf.
*Margins.*—Lobed, serrate, undulating.
*Apex.*—Acuminate.
*Bases.*—Sagittate.
*Thickness.*—Medium.
*Undulation of blade between main and lateral veins.*—Slight.
*Shape of teeth.*—Conical, both sides convex.
*Length of teeth.*—Variable 3–10 mm.
*Ratio length/width of teeth.*—About 3:4.
*General shape of petiole sinus.*—Variable — open (ovate) to closed.
*Tooth at petiole sinus.*—Absent.
*Petiole sinus limited by veins.*—Absent.
*Shape of upper lateral sinus.*—Variable, ½ open, ½ ellipsoid.
*Prostrate hairs between veins on lower surface of blade.*—Absent.
*Erect hairs between hairs on lower surface of blade.*—Absent.
*Prostrate hairs on main veins on lower surface of blade.*—Absent.
*Density of erect hairs on main veins on lower surface of blade.*—Sparse; found only at junctions of main veins.
*Prostrate hairs on main veins on upper surface of blade.*—Absent.
*Autumnal coloration.*—Yellowish: 5Y 8/10.

Upper surface:
*Summer color.*—Dark green: 7.5 GY 4/4 to 4/6.
*Autumn color.*—2.5Y 8/8.
*Surface texture.*—Smooth.
*Surface appearance.*—Dull.
*Goffering of blade.*—Absent.

Lower surface:
*Summer color.*—Dark green: 5GY 6/6 to 6/8.
*Autumn color.*—2.5Y 8/6.
*Anthocyanin coloration of main veins on lower leaf surface.*—Absent.
*Glossiness.*—Low.
*Pubescence.*—Absent.
*Surface texture.*—Smooth.
*Surface appearance.*—Semi-glossy.

Petiole:
*Length of petiole.*—12.3 cm.
*Length of petiole compared to middle vein.*—Considerably shorter.
*Density of prostrate hairs on petiole.*—Absent.
*Density of erect hairs on petiole.*—Absent.
*Shape of base of petiole sinus.*—Half open, ovate.
*Diameter.*—3 mm.
*Color.*—5GY 7/6.

TENDRILS

*Number.*—Bifurcated and trifurcated, forming at most nodes between nodes 5–12. Few thereafter.
*Length.*—22.5 cm.
*Diameter.*—2 mm.
*Texture.*—Smooth.
*Color.*—5GY 7/10.

WOODY SHOOT

Cane:
*Shape.*—Circular to broadly elliptical.
*Internode length.*—About 9.0 cm.
*Width at node.*—About 2.0 cm.
*Cross section.*—Circular.
*Surface.*—Smooth.
*Main color.*—Brown: 5YR 5/6.
*Lenticels.*—Inconspicuous.
*Erect hairs on nodes.*—Absent.
*Erect hairs on internodes.*—Absent.
*Growth of axillary shoots.*—Prolific.

Laterals:
*Shape.*—Circular to broadly elliptical in outline.
*Number.*—Laterals occur at all nodes above node 2.
*Length.*—23–41 cm.
*Diameter.*—4–5 mm.
*Internode length.*—4–6 cm.
*Color.*—5YR 4/6.

Buds:
*Shape.*—Conical.
*Cane bud fruitfulness.*—Basal buds fruitful, 1–2 clusters per shoot.
*Length.*—6 mm.
*Width.*—7 mm.
*Height.*—6 mm.
*Color.*—7.5YR 6/6.
*Time of bud burst.*—Mar. 10, 2003.

FLOWERS

General:
*Flower sex.*—Perfect.
*Position of first flowering nodes.*—$3^{rd}$ or $4^{th}$ node.
*Number of inflorescences per shoot.*—1 or 2.
*Calyptra color.*—5GY 7/8.
*Ovary length.*—2 mm.
*Ovary width.*—1.5 mm.
*Ovary color.*—5GY 4/8.
*Filament length.*—2 mm.
*Filament color.*—2.5GY 8/2.
*Anther length.*—1 mm.
*Anther color.*—2.5GY 8/8.
*Date of full bloom.*—May 9, 2001 in McFarland, Calif.

FRUIT

General:
*Ripening period.*—Early to mid-August at Delano, Calif.
*Date of ripening.*—About Aug. 10, 2001.
*Use.*—Fresh market.
*Keeping quality.*—Very good.
*Resistance.*—Insects: typical of *Vitis vinifera*. Diseases: typical of *Vitis vinifera*.
*Shipping quality.*—Good.
*Date of first harvest.*—Aug. 10, 2001.
*Solids-sugar.*—High, about 20 brix at full maturity.
*Refractometer test.*—24.0 brix.

Cluster:
*Bunch size.*—Large.
*Bunch length* (*peduncle excluded*).—About 27 cm.
*Bunch width.*—About 8 cm.
*Bunch weight* (*natural*).—1291 g.
*Bunch weight* (*gibberellic acid treated*).—1,272 g.
*Bunch density.*—Loose.
*Number of berries.*—75.
*Form.*—Elliptic.

Peduncle:

*Length of peduncle.*—7 cm.

*Lignification of peduncle.*—None.

*Color.*—5GY 5/10.

Berry:

*Size.*—Medium.

*Uniformity of size.*—Variable.

*Berry weight* (*natural*).—4.2 g.

*Berry weight* (*gibberellic acid treated*).—9.4 g.

*Shape.*—Elliptic to oblong.

*Presence of seeds.*—Seedless; 1 or 2 soft, light brown (7.5YR 7/4) stenospermic traces less than 1 mm in length seen in most berries.

*Cross section.*—Circular.

*Dimensions.*—Longitudinal axis about 2.5 cm.; horizontal axis about 1.7 cm.

*Skin color* (*without bloom*).—Light green: 2.5GY 8/6 to 8/8.

*Coloration of flesh.*—Translucent, 2.5GY 8/4.

*Juiciness of flesh.*—Very juicy.

*Berry firmness.*—Very firm.

*Particular flavor.*—Neutral, typical vinifera.

*Bloom* (*cuticular wax*).—Strong.

*Pedicel length.*—12 mm.

*Berry separation from pedicel.*—Moderate.

Skin:

*Thickness.*—Thick.

*Texture.*—Tender.

*Reticulation.*—Absent.

*Roughness.*—Absent.

*Tenacity.*—Tenacious to flesh.

*Tendency to crack.*—Resistant.

What is claimed is:

1. A new and distinct variety of grape plant named '13-21-12' as herein illustrated and described.

* * * * *

MZI Selection 13-21-12